(12) United States Patent
Hartley et al.

(10) Patent No.: US 9,918,823 B2
(45) Date of Patent: Mar. 20, 2018

(54) REINFORCING RING

(75) Inventors: David Ernest Hartley, Wannanup (AU); Edward Graham Mills, Gordon Park (AU)

(73) Assignee: Cook Medical Technologies LLC, Bloomington, IN (US)

( * ) Notice: Subject to any disclaimer, the term of this patent is extended or adjusted under 35 U.S.C. 154(b) by 1126 days.

(21) Appl. No.: 13/377,453

(22) PCT Filed: Feb. 26, 2010

(86) PCT No.: PCT/US2010/025606
§ 371 (c)(1),
(2), (4) Date: Feb. 1, 2012

(87) PCT Pub. No.: WO2010/144162
PCT Pub. Date: Dec. 16, 2010

(65) Prior Publication Data
US 2012/0123523 A1    May 17, 2012

(30) Foreign Application Priority Data
Jun. 10, 2009   (AU) ............................... 2009202301

(51) Int. Cl.
*A61F 2/82* (2013.01)
*A61F 2/07* (2013.01)
(Continued)

(52) U.S. Cl.
CPC .................. *A61F 2/07* (2013.01); *A61F 2/89* (2013.01); *A61F 2002/061* (2013.01);
(Continued)

(58) Field of Classification Search
CPC . A61F 2/07; A61F 2002/075; A61F 2002/061
(Continued)

(56) References Cited

U.S. PATENT DOCUMENTS

| 4,907,336 A | 3/1990 | Gianturco |
| 5,554,181 A * | 9/1996 | Das ............................. 623/1.12 |

(Continued)

FOREIGN PATENT DOCUMENTS

| WO | WO 02/39926 A2 | 5/2002 |
| WO | WO 2005/034808 A1 | 4/2005 |

(Continued)

OTHER PUBLICATIONS

International Search Report—PCT/US2010/025606; dated May 26, 2010, 4 pages.
(Continued)

*Primary Examiner* — Julie A Szpira
(74) *Attorney, Agent, or Firm* — Brinks Gilson & Lione

(57) ABSTRACT

A reinforcing ring (10) for a fenestration (32) of a stent graft which can be surface treated such as by passivation and/or electropolishing. The reinforcing ring has several turns of a substantially inextensible resilient wire (12) in a circular two dimensional planar shape and terminal ends (14) at each end of the wire. The terminal ends each comprising a loop (14) and a tail (16). The tail is folded back and extends around the circular shape. Each of the tails of the terminal loops can have an enlarged end. The reinforcing ring can be straightened out for surface treatment such as passivation and/or electropolishing with substantially no part of the circular shape, the loops or tails touching each other.

9 Claims, 4 Drawing Sheets

(51) Int. Cl.
*A61F 2/89* (2013.01)
*A61F 2/06* (2013.01)

(52) U.S. Cl.
CPC . *A61F 2002/075* (2013.01); *A61F 2220/0075* (2013.01); *Y10T 428/21* (2015.01)

(58) Field of Classification Search
USPC .................. 606/153, 213; 623/1.13, 1.15
See application file for complete search history.

(56) References Cited

U.S. PATENT DOCUMENTS

| | | | |
|---|---|---|---|
| 5,653,743 A | 8/1997 | Martin | |
| 6,030,414 A | 2/2000 | Taheri | |
| 6,355,052 B1* | 3/2002 | Neuss et al. | 606/213 |
| 6,395,018 B1 | 5/2002 | Castaneda | |
| 6,565,581 B1* | 5/2003 | Spence et al. | 606/153 |
| 7,413,573 B2 | 8/2008 | Hartley et al. | |
| 7,608,086 B2 | 10/2009 | Tanaka et al. | |
| 7,645,298 B2* | 1/2010 | Hartley et al. | 623/1.35 |
| 7,766,861 B2* | 8/2010 | Levine et al. | 604/57 |
| 7,914,572 B2 | 3/2011 | Hartley et al. | |
| 8,043,357 B2 | 10/2011 | Hartley | |
| 8,337,546 B2* | 12/2012 | Bruszewski | 623/1.35 |
| 2005/0070934 A1* | 3/2005 | Tanaka et al. | 606/153 |
| 2005/0102021 A1 | 5/2005 | Osborne | |
| 2007/0219621 A1* | 9/2007 | Hartley et al. | 623/1.13 |
| 2008/0312732 A1* | 12/2008 | Hartley et al. | 623/1.13 |
| 2010/0268319 A1* | 10/2010 | Bruszewski et al. | 623/1.13 |
| 2011/0190868 A1* | 8/2011 | Ducke et al. | 623/1.13 |
| 2012/0290068 A1* | 11/2012 | Roeder et al. | 623/1.13 |

FOREIGN PATENT DOCUMENTS

WO   WO 2007/084537 A2   7/2007
WO   WO 2010/030370 A1   3/2010

OTHER PUBLICATIONS

International Written Opinion—PCT/US2010/025606; dated May 26, 2010, 6 pages.

* cited by examiner

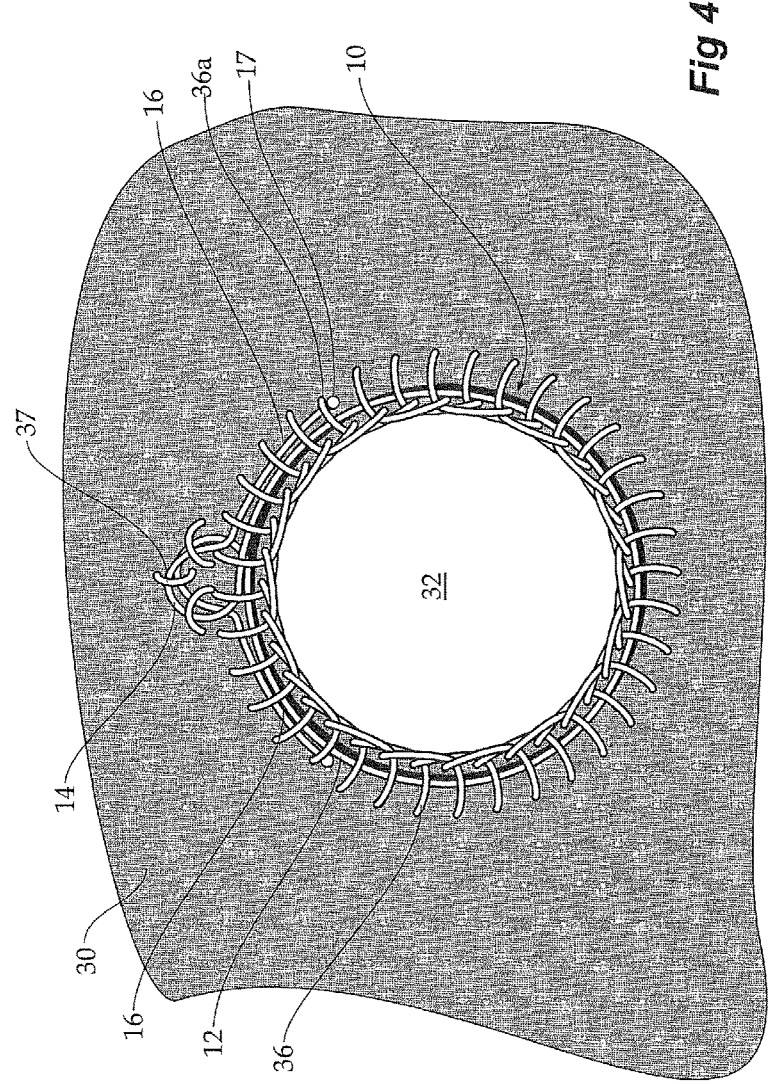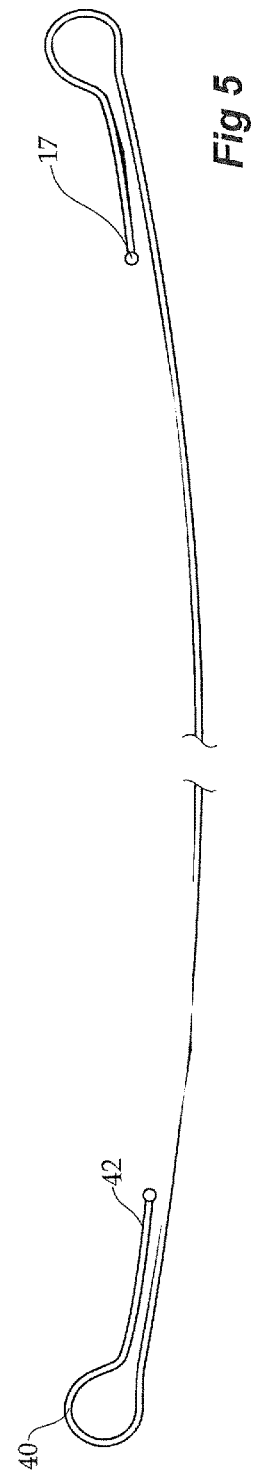

REINFORCING RING

TECHNICAL FIELD

This invention relates to a medical device and more particularly to a reinforcing ring used in stent graft device.

BACKGROUND ART

Stent grafts are used to bridge a defect in the vasculature of a patient and can be deployed into the vasculature endovascularly. This requires that the device can be constrained into a small delivery device and be able to expand or be expanded when release within the vasculature.

Where there are side branches to the vasculature it may be necessary to provide an aperture in the stent graft, known as a fenestration, to enable access from a deployed stent graft to that side branch. Such a fenestration may be reinforced with a peripheral circular ring stitched to the graft material around the fenestration. It is also desirable in some situations to provide a side branch stent graft extending through the fenestration and into the side branch.

PCT Publication WO 2005/034808 entitled "Fenestrated Stent Graft" describes the use of resilient reinforcing rings in stent grafts and the teachings therein are incorporated herein in their entirety.

To obtain a good seal of the branch stent graft within the fenestration an inflatable balloon can be used to expand the branch stent graft into the fenestration and for this purpose the reinforcing ring must be able to resist expansion of its diameter. At the same time the ring must be resilient so that it can be distorted into its deployment configuration but when released expand back to its circular configuration. In this specification the term resilient when used in relation to a wire used to manufacture a reinforcing ring refers to a wire which is substantially inextensible but which has a spring function so that when distorted and released returns to its original configuration.

This invention will be discussed in relation to the application of a reinforcing ring to a fenestration but such a ring may have greater applicability.

Generally such a reinforcing rings is manufactured from a metal known as a superelastic metal such as, but not restricted, to a nickel titanium alloy known as Nitinol. To form a ring of a superelastic metal the desired final shape is formed from a wire on a former and then the wire on the former is heated above a temperature which sets the wire in the new shape. Upon cooling the ring holds it formed shape and can be distorted and resiliently returns to the formed shape.

The reinforcing rings discussed in PCT Publication WO 2005/034808 mentioned above when formed from a resilient wire each have substantially circular loops at the terminal ends of the wire. These loops prevent the sharp end of the wire puncturing the vasculature into which the stent graft is deployed. When it is desired to electropolish rings incorporating these prior art loops it is necessary to straighten out the ring but the prior art loops do not permit efficient electropolishing because parts of the loops touch the wire of the ring.

DISCLOSURE OF THE INVENTION

In one form therefore the invention is said to reside in a reinforcing ring for a fenestration of a stent graft, the reinforcing ring comprising a plurality of turns of a substantially inextensible resilient wire in a circular two dimensional shape and terminal ends at each end of the wire, the terminal ends each comprising a loop and a tail folded back and extending around the circular shape whereby the reinforcing ring can be straightened out for subsequent surface treatment with substantially no part of the circular shape, the loops or tails touching each other.

The substantially inextensible resilient wire can be a superelastic wire such as a wire formed from a nickel titanium alloy such as Nitinol.

The forming of the loop provides an end which is less likely to potentially damage the vasculature or a graft material. The provision of the tail which is folded back and extending around the circular shape enables the subsequent surface treatment to be carried out on all of the surfaces of the wire after it has been straightened out in a substantially linear manner.

Preferably there are substantially two circular turns of the wire.

In preferred embodiments the terminal loops at each end of the wire can overlap or be spaced apart either past each other or nearly reaching each other.

In one embodiment there are two complete circular turns of the wire and the loops extend further around the circular shape.

In one embodiment the terminal loops at each end of the wire can extend out of the plane of the circular shape at approximately right angles thereto.

In one embodiment each of the tails of the terminal loops comprises an enlarged end. The enlarged end can be in the form of a ball of solder or the like.

The subsequent surface treatment such may be polishing, passivation or coating. The polishing may be electropolishing, mechanical polishing or chemical polishing. According to the present invention these processes can be carried out on the entire surface of the reinforcing ring of the present invention because when it is straightened out no part of the loops or tails touch each other.

The process of passivation in relation to a nickel titanium alloy is intended to provide a protective nickel-depleted titanium rich oxide layer for good biocompatibility. Passivation also improves the corrosion resistance of the surface.

Electropolishing, also referred to as electrochemical polishing, is an electrochemical process that removes material from a metallic workpiece. It is used to polish, passivate and deburr metal parts. It is often described as the reverse of electroplating. It differs from anodizing in that the purpose of anodizing is to grow a thick, protective oxide layer on the surface of a material (usually aluminum) rather than polish.

For electropolishing typically, a metal work piece is immersed in a temperature controlled bath of electrolyte and connected to the positive terminal of a DC power supply, the negative terminal being attached to an auxiliary electrode. A current passes from the anode where metal on the surface is oxidized and dissolved in the electrolyte. At the cathode, a reduction reaction, normally hydrogen evolution, takes place. Electrolytes used for electropolishing are most often concentrated acid solutions having a high viscosity such as mixtures of sulfuric acid and phosphoric acid. Other electropolishing electrolytes reported in the literature include mixtures of perchlorates with acetic anhydride and methanolic solutions of sulfuric acid. To achieve electropolishing of a rough metal surface, the protruding parts of a surface profile must dissolve faster than the recesses. This behavior (referred to as anodic leveling) is achieved by applying a specific electrochemical condition, most often involving a mass transport limited dissolution reaction. A second condition for achieving polishing is that surface heterogeneities due to crystal orientation in a polycrystalline material are suppressed and that no pitting occurs. These conditions, often associated with surface brightening, are usually fulfilled with the above mentioned polishing electrolytes and with proper process control. Anodic dissolution under electropolishing conditions deburrs metal objects due to increased current density on corners and burrs.

Hence in the present invention, the reinforcing ring after it has been formed and suitably heat treated, as discussed above, so that it will return to its circular ring shape can be stretched out into a linear form so that no part of the ring touches another and then can be electrochemically polished or have some other surface treatment applied. Upon being released from its straightened out condition the ring will return to its circular ring shape.

BRIEF DESCRIPTION OF THE DRAWINGS

This then generally describes the invention but to assist with understanding reference will now be made to the accompanying drawings which show preferred embodiments of the invention.

In the drawings:

FIG. 4 shows a reinforcing ring according to the embodiment shown in FIG. 2 stitched into a portion of graft material;

FIG. 5 shows a reinforcing ring according to the embodiments shown in FIGS. 1 to 3 stretched out for electropolishing;

DESCRIPTION OF PREFERRED EMBODIMENTS

Figure 1:
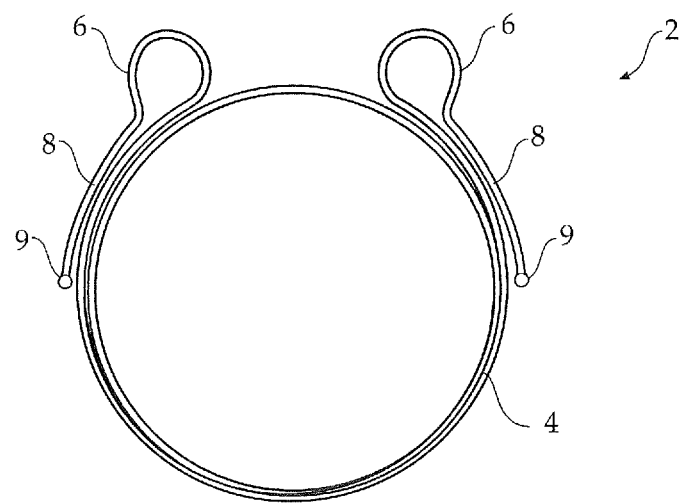
FIG. 1 shows a first embodiment of a reinforcing ring of the present invention.

Now looking more closely at the drawings and in particularly the embodiment shown in FIG. 1 it will be seen that the reinforcing ring 2 is formed into a two dimensional circular shape of a superelastic wire 4. The ring has a diameter of from 5 to 15 mm when it is used as a reinforcing ring for a fenestration and from 10 to 40 mm when it is used as an end reinforcement for a tubular stent graft. The ring 2 is formed from a superelastic metal wire such as a nickel titanium alloy such as Nitinol. The wire can have a diameter of from 0.1 mm to 1 mm and preferably a diameter of from 0.15 mm to 0.3 mm.

The ring has nearly two turns of the wire 4 and each end of the wire terminates in a loop 6 and a tail 8. The loop 6 is generally of a diameter through which can be passed a needle during stitching of the reinforcing ring into a graft material. Typically the loops may have a diameter of from 1 mm to 2 mm. The tail 8 extends back around the periphery of the reinforcing ring and when the wire is stretched out for passivation and/or electropolishing the tails are slightly spaced away from it (see FIG. 5). After electropolishing or other surface treatment and when the reinforcing ring is stitched into a stent graft there is no problem with the parts of the ring touching each other.

Each of the tails 8 ends in an enlarged end 9. The enlarged end 9 can be for instance in the form of a ball formed from solder, fused material of the ring of the like. The enlarged end is provided to protect the fabric of a stent graft unto which the reinforcing ring is mounted from the sharp points at the ends of the wire and to assist the sewing of the end of the wire as a stitch can be added next to the ball which stitch can engage against the enlarged end or ball and prevents the wire from being pulled in one direction.

Figure 2:
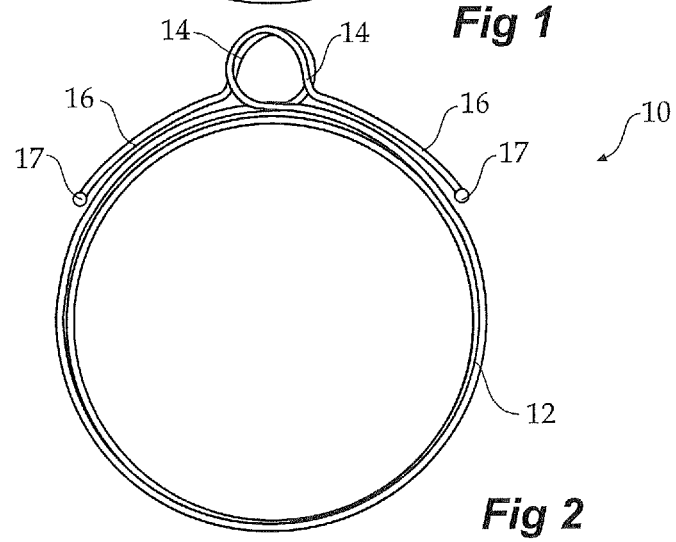
FIG. 2 shows an alternative embodiment of a reinforcing ring of the present invention.

FIG. 2 shows an alternative embodiment of reinforcing ring according to the invention. The reinforcing ring 10 is formed into a two dimensional circular shape of a superelastic wire 12. The ring 10 has two turns of the wire 12 and each end of the wire terminates in a loop 14 and a tail 16. The loops 14 overlap each other. The tails 16 extend back around the periphery of the reinforcing ring and when the wire is stretched out for passivation and/or electropolishing the tails are slightly spaced away from it (see FIG. 5). Each of the tails 16 ends in an enlarged end 17.

Figure 3:
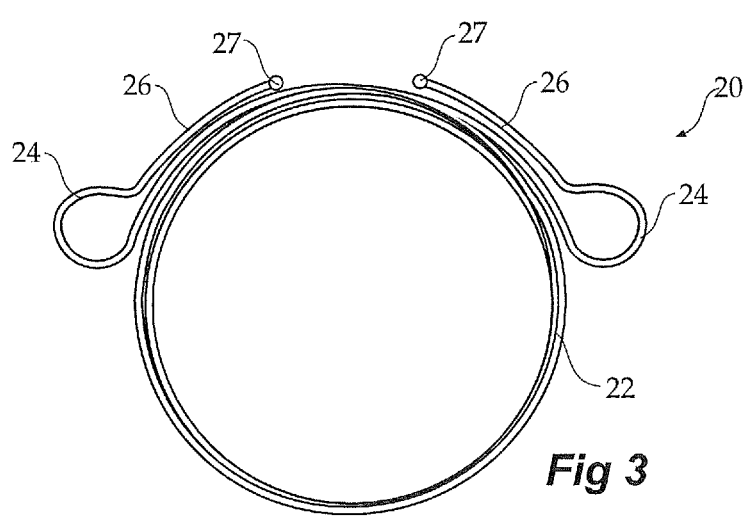
FIG. 3 shows an alternative embodiment of a reinforcing ring of the present invention.

FIG. 3 shows an alternative embodiment of reinforcing ring according to the invention. The reinforcing ring 20 is formed into a two dimensional circular shape of a superelastic wire 22. The ring 20 has two complete turns and a little more of the wire 22 and each end of the wire terminates in a loop 24 and a tail 26. The tails 26 extend back towards each other. The tails 26 extend back around the periphery of the reinforcing ring and when the wire is stretched out for passivation and/or electropolishing the tails are slightly spaced away from it (see FIG. 5). Each of the tails 26 ends in an enlarged end 27.

FIG. 4 shows a reinforcing ring according to the embodiment shown in FIG. 2 stitched into a portion of graft material. The graft material 30 has a fenestration 32 and around the fenestration is a reinforcing ring 10 retained in place by blanket type stitching 36. In this embodiment the reinforcing ring 10 is of the type shown in FIG. 2 and the loops 14 overlap and two of the stitches of the stitching pass through the loops 14. These extra stitches 37 are provided into the loops 14 and through the graft material. The tails 16 are also retained within the stitches 36. It will be noted in particular that the stitch 36a engages against the enlarged end or ball 17.

FIG. 5 shows a reinforcing ring according to the embodiments shown in FIGS. 1 to 3 stretched out for passivation and/or electropolishing. The wire 40 is stretched essentially by pulling upon the tails 42 at each end out so that no portion of the rings, loops or tails touch another. It will be particularly noted that when stretched out the tail 42 does not touch the wire 40 thereby ensuring good electropolishing all over the wire.

Figure 6:
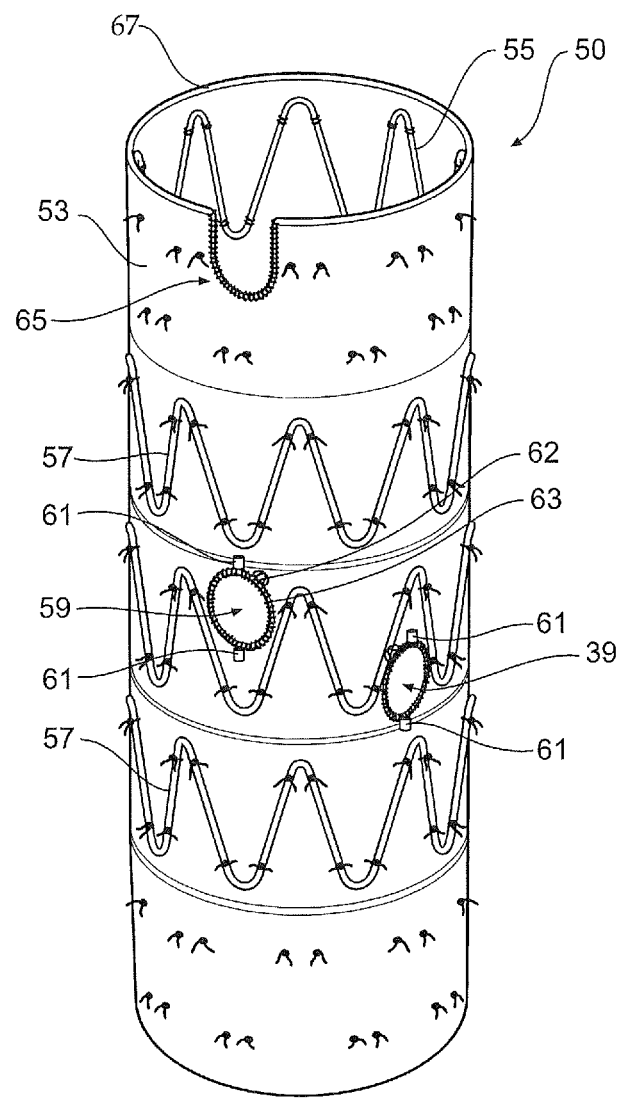
FIG. 6 shows a stent graft incorporating fenestrations and a reinforcing ring according to the present invention.

FIG. 6 shows a stent graft incorporating fenestrations and a reinforcing ring according to the present invention. A stent graft 50 comprises a tubular wall body portion 53. The tubular wall body portion is a biocompatible graft material such as Dacron, Thoralon, expanded PTFE material or a naturally occurring biomaterial, such as an extracellular matrix, such as small intestinal submucosa or other suitable material.

Gianturco style zig zag Z stents 55 are provided inside the graft material at each end and on the central tubular wall body portion Gianturco style zig zag Z stents 57 are provided on the outside of the graft material. There may be further Gianturco style zig zag Z stents than those illustrated depending upon the overall length of the stent graft 50. Other forms of stent may also be used.

In the tubular wall body portion 53 there are two substantially circular fenestrations or apertures 59 on the tubular wall of the stent graft. In this embodiment there are two fenestrations being one for each of the two renal arteries when this embodiment is deployed into the aorta. Other numbers of fenestrations may also be used where the placement of the stent graft involves the possibility of occluding other branch vessels such as the superior mesenteric artery and the celiac artery. The fenestrations 59 are substantially circular. Radiopaque markers 61 are provided at each end of the fenestration 59 to assist a physician to locate the fenestration 59 in respect to a side vessel extending from a main vessel. The radiopaque markers 61 may be gold or other convenient material.

A reinforcement ring 62 of the present invention is provided around the periphery of the fenestration 59 to give good dimensional stability to the fenestration 59. The reinforcing ring is manufactured from Nitinol wire. In an alternative arrangement the ring 62 may be formed from stainless steel or any other convenient material. Stitching 63 is provided to retain the ring 62 around the periphery of the fenestration 59.

Also in FIG. 6 there is shown a scalloped fenestration 65 which opens to the end 67 of the stent graft.

Figure 7:
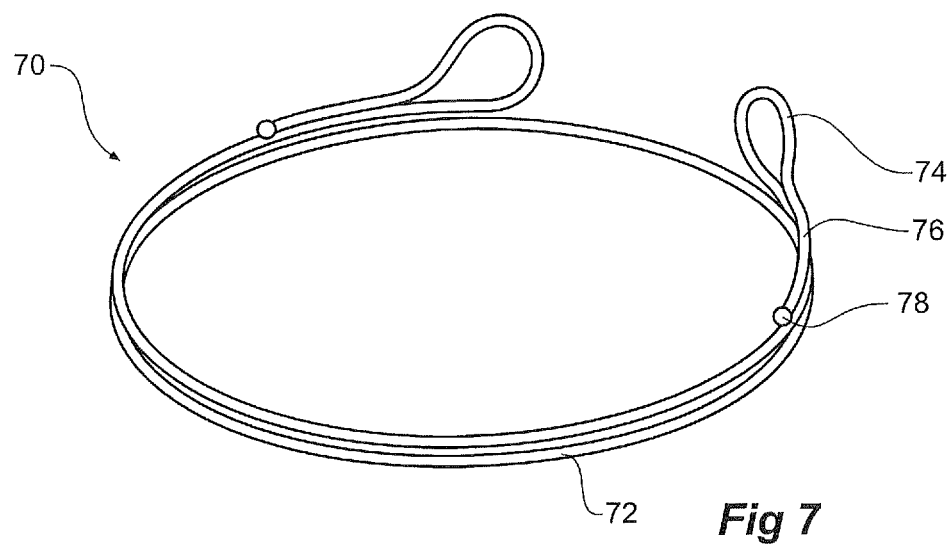
FIG. 7 shows an alternative embodiment of the invention.

FIG. 7 shows an alternative embodiment of the invention. In this embodiment the reinforcing ring 70 has nearly two full turns of Nitinol wire 72 and each end of the wire terminates in a loop 74. Each of the loops extend out of the plane of the circular shape at approximately right angles thereto. The tails 76 of the loops extend around the periphery of the circular shape and each of the tails 76 ends in an enlarged end 78.

The reinforcement ring of this embodiment is useful as a reinforcing ring at the end of a tubular body of graft material such as an arm or leg of a stent graft where the ring is stitched around the end of the tubular body and the loops at right angles to the plane of the ring extend along the tubular body and can be stitched thereto.

Figure 8:
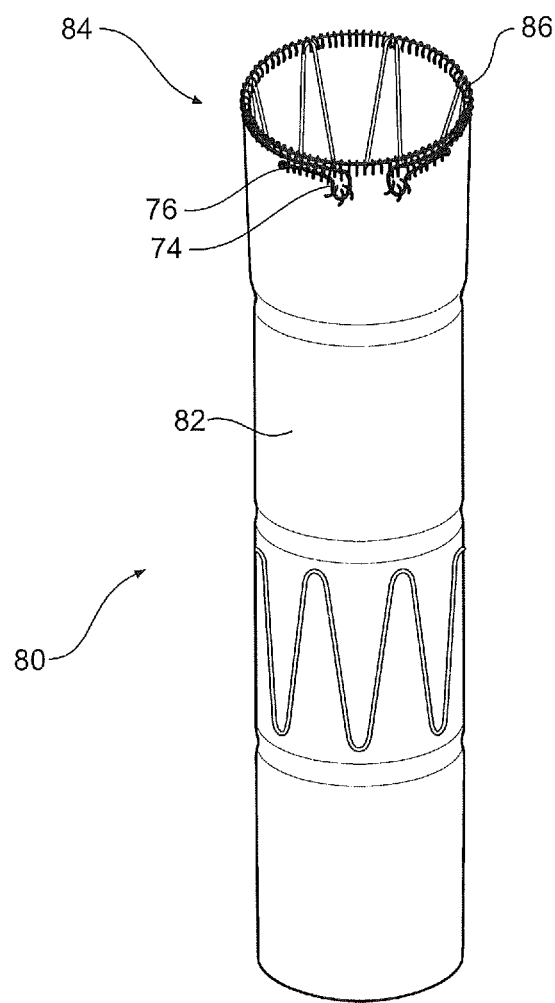
FIG. 8 shows a leg extension stent graft incorporating a ring reinforcement of the embodiment of FIG. 7.

FIG. 8 shows a leg extension stent graft incorporating a ring reinforcement of the embodiment of FIG. 7. In FIG. 8 the leg extension 80 has a tubular body 82 of a graft material and a reinforcement ring 70 at its proximal end 84. The ring has loops 74 which extend out of the plane of the circular shape of the ring at approximately right angles and along the side of the tubular body. Stitching 86 fastens the ring to the tubular body and also some of the stitches pass through the loops 74 and over the tails 76.

Throughout this specification various indication have been made as to the scope of the invention but the invention is not limited to any one of these but may reside in more than one combined together. The example and embodiments are given for illustration only and not for limitation.

The invention claimed is:

1. A reinforcing ring for a fenestration of a stent graft, the reinforcing ring comprising a plurality of turns of a substantially inextensible resilient wire in a circular two dimensional planar shape and terminal ends at each end of the wire, the terminal ends each comprising a loop and a tail, the tail extending from the loop, the tail being folded back and extending around the circular shape.

2. A reinforcing ring as in claim 1 wherein the substantially inextensible resilient wire comprises a superelastic wire.

3. A reinforcing ring as in claim 1 wherein the wire comprises a nickel titanium alloy.

4. A reinforcing ring as in claim 1 wherein there are approximately two circular turns of the wire.

5. A reinforcing ring as in claim 1 wherein the terminal loops at each end of the wire overlap.

6. A reinforcing ring as in claim 1 wherein there are two complete circular turns of the wire and the loops extend further around the circular shape.

7. A reinforcing ring as in claim 1 wherein the terminal loops at each end of the wire extend out of the plane of the circular shape at approximately right angles thereto.

8. A reinforcing ring as in claim 1 wherein each of the tails of the terminal loops comprises an enlarged end.

9. A reinforcing ring for a fenestration of a stent graft, the reinforcing ring comprising a plurality of turns of a substantially inextensible resilient wire in a circular two dimensional planar shape and terminal ends at each end of the wire, the terminal ends each comprising a loop and a tail, the tail extending from the loop, the tail being folded back and extending around the circular shape, each of the tails of the terminal loops comprises an enlarged end and the wire comprising a passivated or extropolished surface or a passivated and electropolished surface.

* * * * *